US010482996B2

United States Patent
Wlodarczyk et al.

(10) Patent No.: US 10,482,996 B2
(45) Date of Patent: Nov. 19, 2019

(54) SYSTEMS AND METHODS FOR DETERMINING RELATIVE GEOCHEMICAL DATA

(71) Applicant: Schlumberger Technology Corporation, Sugar Land, TX (US)

(72) Inventors: Sylvain Wlodarczyk, Saint-Clément-de-Rivière (FR); Gennady Makarychev, Castelnau-le-Lez (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 968 days.

(21) Appl. No.: 14/267,042

(22) Filed: May 1, 2014

(65) Prior Publication Data

US 2014/0330518 A1 Nov. 6, 2014

(30) Foreign Application Priority Data

May 6, 2013 (FR) ..................... 13 54150

(51) Int. Cl.
*G06F 19/00* (2018.01)
*G16C 20/20* (2019.01)
*G01V 9/00* (2006.01)

(52) U.S. Cl.
CPC ............... *G16C 20/20* (2019.02); *G01V 9/00* (2013.01)

(58) Field of Classification Search
CPC ......... G06F 19/703; G06F 19/00; G01V 9/00; G01N 33/24
See application file for complete search history.

(56) References Cited

U.S. PATENT DOCUMENTS

| 5,440,118 A * | 8/1995 | Roscoe ................. G01V 5/101 250/262 |
| 7,805,250 B2 | 9/2010 | Colombo et al. |
| 8,213,261 B2 | 7/2012 | Imhof et al. |
| 8,447,524 B2 | 5/2013 | Chen et al. |
| 8,498,848 B2 | 7/2013 | Habashy et al. |

(Continued)

OTHER PUBLICATIONS

Galford, et aL, "A New Neutron-Induced Gamma-Ray Spectroscopy Tool for Geochemical Logging," SPWLA 50th Annual Logging Symposium, Jun. 21-24, 2009.

(Continued)

*Primary Examiner* — Mohamed Charioui
*Assistant Examiner* — Jeremy A Delozier (57) ABSTRACT

Systems, media, and methods for determining relative geochemical data are provided. Measurement data may be received that is indicative of relative yields of a plurality of chemical components in a rock formation. First absolute yields of at least a portion of the plurality of chemical components in a presence of 100% of a first volumetric component in the rock formation may be determined. Second absolute yields of at least a portion of the plurality of chemical components in a presence of 100% of a second volumetric component in the rock formation may also be determined. A volume of the first volumetric component, a volume of the second volumetric component, and a sum of yields of the plurality of chemical components may be determined using the first and second absolute yields and the relative yields.

21 Claims, 5 Drawing Sheets

(56) References Cited

U.S. PATENT DOCUMENTS

2010/0312479 A1* 12/2010 Khisamutdinov .. E21B 47/1015
  702/8
2011/0002194 A1*  1/2011 Imhof ..................... G01V 1/32
  367/53
2011/0022320 A1*  1/2011 Abousleiman ........ E21B 49/006
  702/12
2011/0040536 A1   2/2011 Levitan

OTHER PUBLICATIONS

Quirein, et al., "A Coherent Framework for Developing and Applying Multiple Formation Evaluation Models," SPWLA 27th Annual Logging Symposium, Jun. 9-13, 1986.

Quirein, et al., "Enhancements to the Pulsed Neutron Gamma Ray Spectroscopy Interpretation Process," SPWLA 28th Annual Logging Symposium, Jun. 29-Jul. 2, 1987.

Radtke, et aL, "A New Capture and Inelastic Spectroscopy Tool Takes Geochemical Logging to the Next Level," SPWLA 53rd Annual Logging Symposium, Jun. 16-20, 2012.

* cited by examiner

SYSTEMS AND METHODS FOR DETERMINING RELATIVE GEOCHEMICAL DATA

CROSS-REFERENCE TO RELATED APPLICATIONS

This application claims priority to French Patent Application having serial number 1354150, which was filed on May 6, 2013 and is incorporated by reference herein its entirety.

BACKGROUND

The volume of one or more compounds (e.g., quartz and calcite) in a rock formation may be calculated if the chemical and/or mineral components (e.g., elements) in the rock formation are known. The equations for this relationship are:

$$Y_{silicon} = (0)(V_{calcite}) + (P_{sil})(V_{quartz})$$

$$Y_{calcium} = (P_{cal})(V_{calicite}) + (0)(V_{quartz})$$

where represents the yield of the chemical component silicon, $Y_{calcium}$ represents the yield of the chemical component calcium, $P_{sil}$ represents the proportion of silicon in quartz ($SiO_2$) mineral, $P_{cal}$ represents the proportion of calcium in calcite ($CaCO_3$) mineral, $V_{calcite}$ is the volume of calcite, and $V_{quartz}$ is the volume of quartz.

The current implementation of geochemical log processing provides relative yields of the chemical components defined as the ratio of the yields of the chemical components. For example, the equation may be $$RY_{CA} = \frac{Y_{calcium}}{Y_{silicon} + Y_{calcium} + \ldots + Y_{background}}$$

where $RY_{CA}$ represents the relative yield of calcium.

The algebraic simplification of this method may lead to inconsistency when fluids or other chemical components (e.g., elements) that are not described by the relative yields are introduced in the inversion system. Those fluids and components may then be overestimated. Additionally, the weighted vector mix of the relative yields in the denominator may lead to confusion when analyzing the results of reconstructed yields from the inversion.

SUMMARY

Systems, media, and methods for determining relative geochemical data are disclosed. Measurement data may be received that is indicative of relative yields of a plurality of chemical components in a rock formation. First absolute yields of at least a portion of the plurality of chemical components in a presence of 100% of a first volumetric component in the rock formation may be determined. Second absolute yields of at least a portion of the plurality of chemical components in a presence of 100% of a second volumetric component in the rock formation may also be determined. A volume of the first volumetric component, a volume of the second volumetric component, and a sum of yields of the plurality of chemical components may be determined using the first and second absolute yields and the relative yields.

It will be appreciated that the foregoing summary is merely intended to introduce a subset of the subject matter discussed below and is, therefore, not limiting.

BRIEF DESCRIPTION OF THE DRAWINGS

The accompanying drawings, which are incorporated in and constitute a part of this specification, illustrate embodiments of the present teachings and together with the description, serve to explain the principles of the present teachings. In the figures.

DETAILED DESCRIPTION

The following, detailed description refers to the accompanying drawings. Wherever convenient, the same reference numbers are used in the drawings and the following description to refer to the same or similar parts. While several embodiments and features of the present disclosure are described herein, modifications, adaptations, and other implementations are possible, without departing from the spirit and scope of the present disclosure.

The relative yields of mineral and/or chemical components e.g., calcium, as shown below) in a rock formation may be described by equation (1):

$$RY_{CA} = \frac{Y_{ca}}{Y_{si} + Y_{ca} + \ldots Y_{fe} + \ldots + Y_{gd}} \quad (1)$$

where $RY_{CA}$ represents the relative yield of calcium, $Y_{ca}$ represents the yield of the chemical component calcium, $Y_{si}$ represents the yield of the chemical component silicon, $Y_{fc}$ represents the yield of the chemical component iron, and $Y_{gd}$ represents the yield of the chemical component gadolinium. Each chemical component may be measured by a downhole logging tool (e.g., a spectroscopy tool). Although four chemical components are shown in equation (1), it will be appreciated that equation (1) may be used with more or fewer chemical components, depending on the components present in the rock formation and measured by the logging tool.

Figure 1:
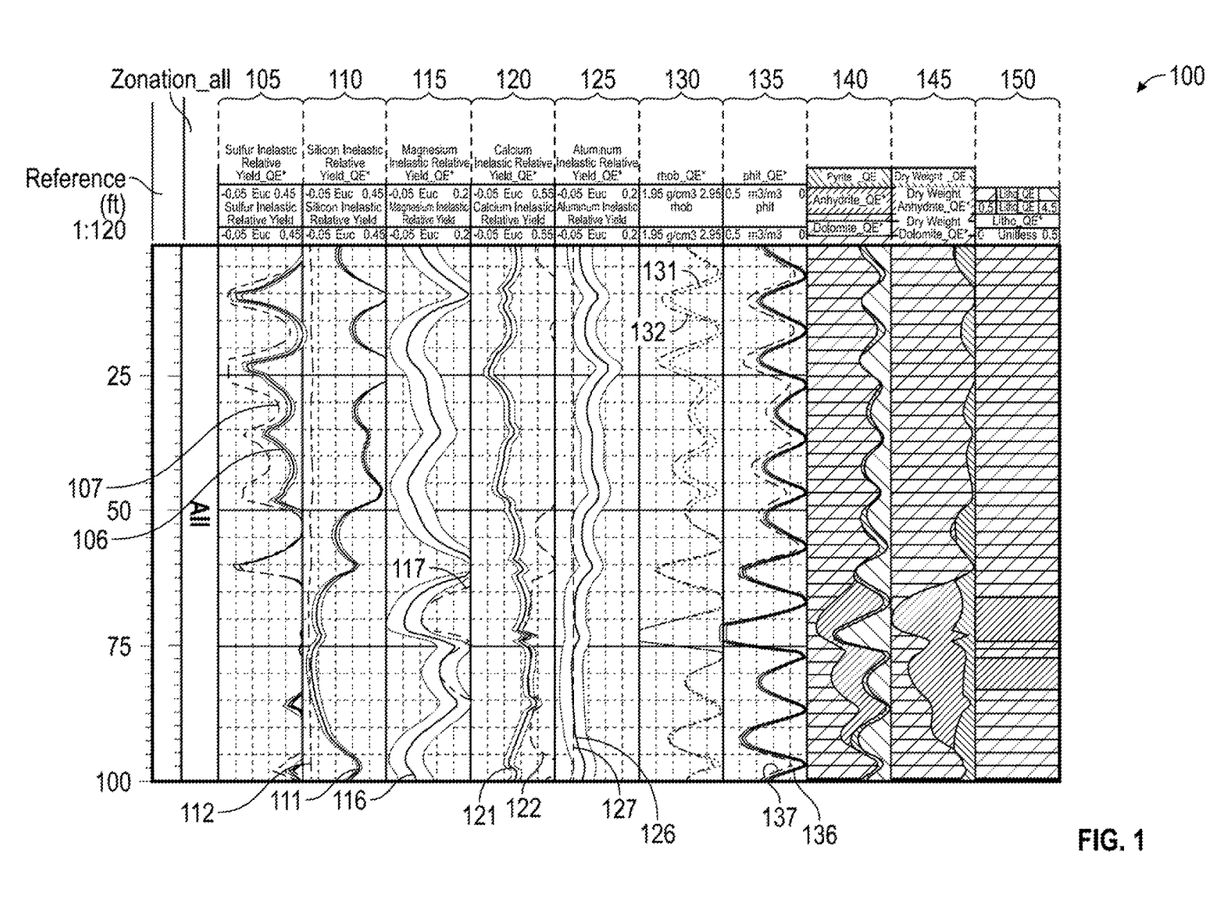
FIG. 1 illustrates a geochemical log model where one or more chemical components are modified to introduce inconsistency, according to an embodiment.

FIG. 1 illustrates one specific example of a geochemical log model 100 for an initial data set where one or more chemical components are modified to introduce inconsistency, according to an embodiment. The geochemical log model 100 may be a "forward" model that estimates logs based on known volumes of components (e.g., minerals and fluids).

The first column 105 represents the relative yield of sulfur. The curve 106 represents the sulfur input, and the curve 107 represents the sulfur reconstruction, for example, from an inversion model. The inversion model may estimate volumes of the components (e.g., minerals and fluids) from log data. The second column 110 represents the relative yield of silicon. The curve 111 represents the silicon input, and the curve 112 represents the silicon reconstruction from the inversion model. The third column 115 represents the relative yield of magnesium. The curve 116 represents the magnesium input, and the curve 117 represents the magnesium reconstruction from the inversion model. The fourth column 120 column represents the relative yield of calcium. The curve 121 represents the calcium input, and the curve 122 represents the calcium reconstruction from the inversion model. The fifth column 125 represents the relative yield of aluminum. The curve 126 represents the aluminum input, and the curve 127 represents the aluminum reconstruction from the inversion model.

The sixth column 130 represents the bulk density of the rock formation. The curve 131 represents the hulk density input, and the curve 132 represents the bulk density reconstruction from the inversion model. The seventh column 135 represents the porosity of the rock formation. The curve 136 represents the porosity input, and the curve 137 represents the porosity reconstruction from the inversion model. The eighth column 140 represents the resulting volumetric model, the ninth column 145 represents the resulting matrix, model, and the tenth column 150 represents the lithology of the model. It will be appreciated that the order of the columns 105, 110, 115, 120, 125, 130, 135, 140 (and others) may be changed to any other order, and/or may include any other suitable columns of information, without departing from the scope of the present disclosure.

Using equation (1), an initial geochemical log model may be computed and constructed. The chemical components may be modified to introduce inconsistency in the initial model. More particularly, the source of silicon (e.g., in column 110) may be removed, and the quartz may be removed in columns 140, 145, 150. As porosity may be independent of the geochemical data, the reconstruction may not be affected. However, the geochemical log model 100 in FIG. 1 shows that the reconstruction may be affected when equation (1) is used. For example, as may be seen in column 135 (representing porosity of the rock), the reconstruction may be affected as evidenced by the porosity reconstruction curve 137 not being aligned (i.e., not overlaying) the porosity input curve 136).

Accordingly, the denominator in equation (1) may be replaced by a single unknown variable (e.g., "B") that represents a sum of the yields of the chemical components, as shown in equation (2):

$$B = Y_{si} + Y_{ca} + Y_{fe} + \ldots + Y_{gd} \qquad (2)$$

Combining equations (1) and (2) results in $$RY_{CA} = \frac{(R_{ca})(V)}{B} \qquad (3)$$

where $R_{ca}$ is an "absolute yield" or absolute measurement value of chemical components (elements) in the presence of 100% of a given volumetric component V. As the term is used herein, "absolute yield" generally refers to the amount (e.g., percentage) of a particular chemical component in the presence of a volume made up (100%) of a rock (e.g., calcite or quartz) having a known chemical composition. For example, the chemical composition of calcite is known ($CaCO_3$). From this, the absolute yields of the constituent elements of calcite, namely, calcium, carbon, and oxygen, that would be measured, if the volumetric component being measured was made of 100% calcite, may be determined. These absolute yields can be stored in and retrieved from a database, calculated on-the-fly (i.e., "just-in-time") during other operations, or otherwise determined.

The unknown variables to solve in the inverse problem are the volumes (of minerals and fluids) and B. For each relative yield, the equation may be represented as:

$$B = \frac{(R_{ca})(V)}{RY_{ca}} = \ldots = \frac{(R_{si})(V)}{RY_{si}} = \frac{(R_{Sul})(V)}{RY_{sul}} \qquad (4)$$

The volumes (V) remain unknown, but the upper limit of B may be estimated by equation (5):

$$0 < B \leq \min\left(\max\left(\frac{(R_i)(V)}{RY_i}\right)\right) \qquad (5)$$

where $R_i$ represents a particular chemical component absolute yield recomputed from volumetric model components, and $RY_i$ represents the relative yield of that particular chemical component from an input data. The volume V may, in some cases, be assumed to be 1, leaving $R_i$ as the numerator in equation (5). The maximum of $R_i/RY_i$ may be determined, for each of a plurality of chemical components, and then the smallest (minimum) of these maximums may be identified.

Equation 5 may be explained using an example. An illustrative formation may include two volumes: V1 and V2 where:

$$V_1 + V_2 = 1 \qquad (6)$$

Both volumes ($V_1$ and $V_2$ may be assumed to be positive. Two illustrative relative yield values $RY_1$ and $RY_2$ may be known from process measurements and be inputs in the inversion system.

$$RY_1 = 0.2 \qquad (7)$$

$$RY_2 = 0.45 \qquad (8)$$

The absolute yields for two chemical components (1) and (2) may also be calculated, or predetermined and retrieved from the database, for example:

|       | $V_1$ | $V_2$ |
|-------|-------|-------|
| $R_1$ | 1     | 2     |
| $R_2$ | 6     | 2     |

Thus, the system to solve may be:

$$RY_1 = \frac{(1)(V_1) + (2)(V_2)}{B} = 0.2 \qquad (9)$$

$$RY_2 = \frac{(6)(V_1) + (2)(V_2)}{B} = 0.45 \qquad (10)$$

B for each equation (9), (10) may be:

$$B = \frac{(1)(V_1) + (2)(V_2)}{0.2} \qquad (11)$$

-continued $$B = \frac{(6)(V_1) + (2)(V_2)}{0.45} \quad (12)$$

In equation (11), B is maximized when $V_1=0$ and $V_2=1$. This leads to:

$$B_{maxeq1} = \frac{(1)(V_1) + (2)(V_2)}{0.2} = \frac{(1)(0) + (2)(1)}{0.2} = 10 \quad (13)$$

In this example case, there is no existing (valid) solution where B may be greater than 10. In equation (12), B is maximized when $V_1=1$ and $V_2=0$. This leads to:

$$B_{maxeq2} = \frac{(6)(V_1) + (2)(V_2)}{0.45} = \frac{(6)(1) + (2)(0)}{0.45} = 13.33 \quad (14)$$

Accordingly, in this example, there is no existing (valid) solution where B may be greater than 13.33.

Once the maximum values of B (e.g., 10 and 13.33) have been calculated for each relative yield (e.g., $RY_1$ and $RY_2$), the smallest maximum value (i.e., the minimum) of B (e.g., 10) may be selected to help identify the maximum limit of B in equation (5). Inserting B=10 as the upper limit in equation (5) provides: $0 < B \leq 10$.

At this point, there are three equations (6), (11), and (12), and three unknowns $V_1$, $V_2$, and B. As such, the three unknowns may be solved for $V_1=0.4$, $V_2=0.6$, and B=8. The model may not be valid if B is outside the limits $0 < B \leq 10$.

Figure 2:
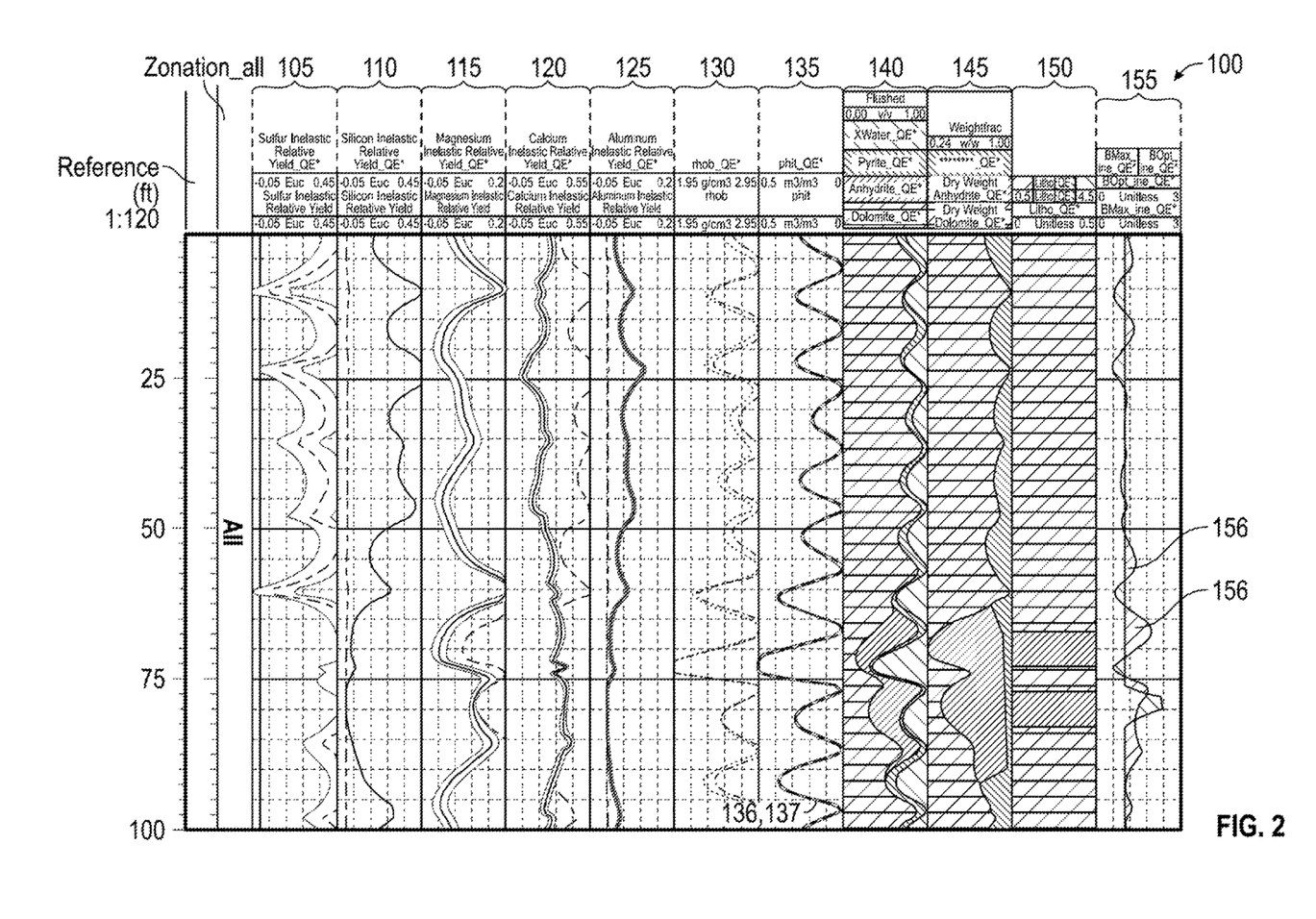
FIG. 2 illustrates the geochemical log model shown in FIG. 1 after being solved using an illustrative (referred to herein as the "B method") inversion system, according to an embodiment.

FIG. 2 illustrates the geochemical log model 100 shown in FIG. 1 after being solved using the "B method" inversion system described above, according to an embodiment. Columns 105-150 may represent the same type of data as in FIG. 1. An eleventh column 155 has been added to FIG. 2 that represents a quality check curve.

The upper limit of B (e.g., 10) may be plotted against the B solved for during the inversion calculation (e.g., 8) to flag the intervals where the model is inconsistent (e.g., due to one or more missing chemical components). The flags 156 in the eleventh column 155 indicate that the mineral components selection may not be valid. This suggests that the mineral model 100 may not be solved for "B," and thus, input geochemical logs (e.g., columns, 105-125) may not be reconstructed. In other words, the model 100 is inconsistent and may be adjusted to add one or more missing chemical components, which may allow the input geochemical logs (e.g., columns, 105-125) to be reconstructed.

FIG. 2 also illustrates that the porosity log (e.g., column 135) may be independent from geochemical logs (e.g., columns 105-125) when the B method is used. For example, while the input and reconstruction porosity curves 136 and 137 are at least partially misaligned in FIG. 1, it may be seen that the curves 136, 137 are now substantially overlapping in column 135 of FIG. 2. This may indicate that the solution is not affected by components that are not described by the geochemical logs (e.g., water).

Figure 3:
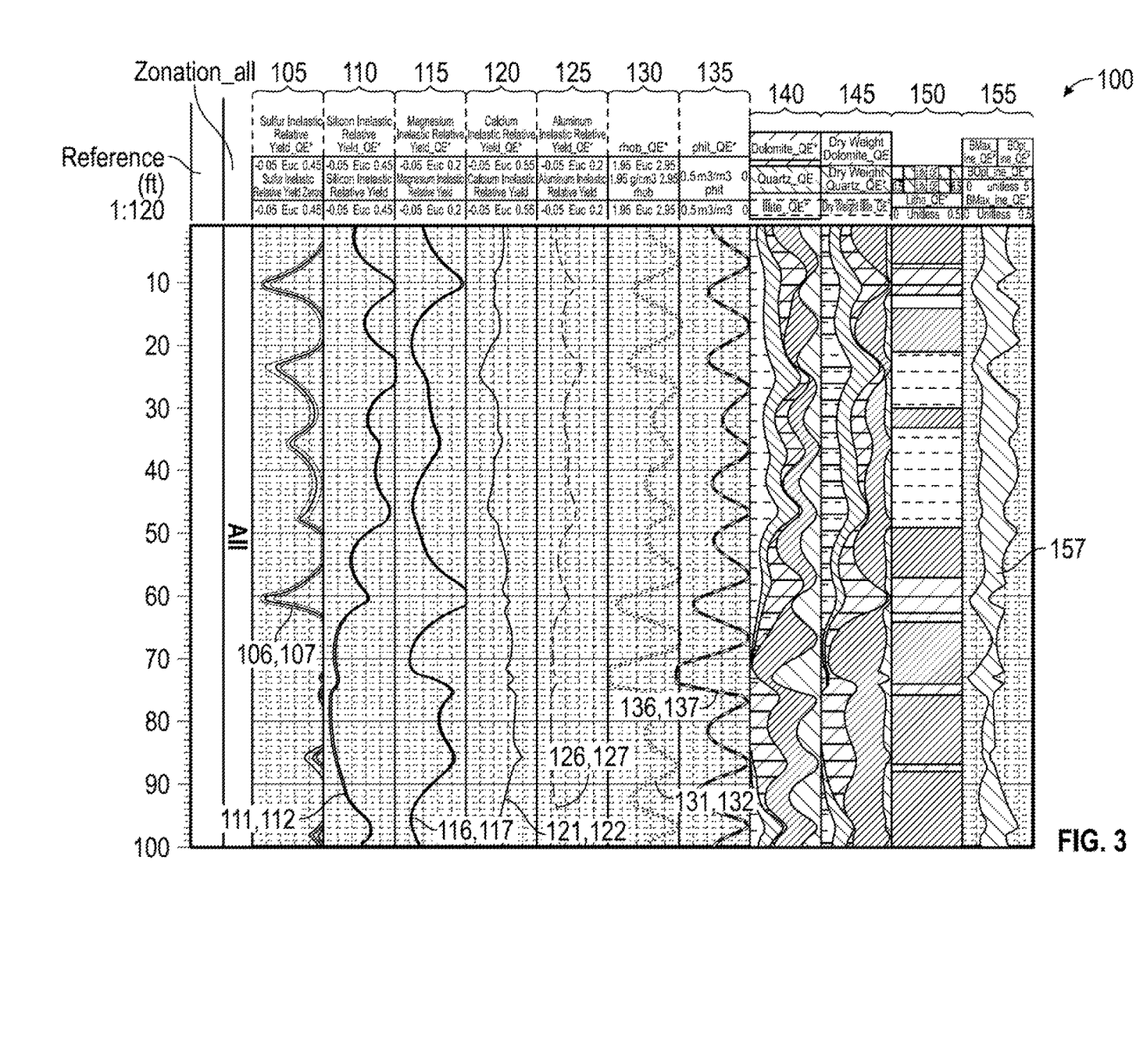
FIG. 3 illustrates the geomechanical log model shown in FIGS. 1 and 2 after a missing component is added, and the model is solved using the B method inversion system, according to an embodiment.

FIG. 3 illustrates the geomechanical log model 100 shown in FIGS. 1 and 2 after one or more missing components are added, and the model 100 is solved using the B method inversion, according to an embodiment. The missing mineral components (e.g., quartz) ma be added to the model 100 (e.g., in columns 140-150). The relative yields (e.g., columns 105-125), the hulk density (e.g., column 130), and the porosity (e.g., column 135) may then be reconstructed. As shown, the input and reconstruction curves (e.g., curves 106, 107, 111, 112, 116, 117, 121, 122, 126, 127, 131, 132, 136, 137) in each column (e.g., columns 105-135) may substantially overlap with one another. Further, the flags 156 in column 155 of FIG. 2, indicating that the mineral components selection may not be valid, are not present in the example shown in FIG. 3. Instead, the flags 156 are replaced by one or more flags 157 in column 155, indicating that the mineral components selection may be valid.

Introducing the unknown variable B in the multi-component inversion system may prevent the fluids and other chemical components that are not described by the relative yields (e.g., $RY_{CA}$) from being overestimated. In addition, the relative yields may not be mixed together.

Figure 4:
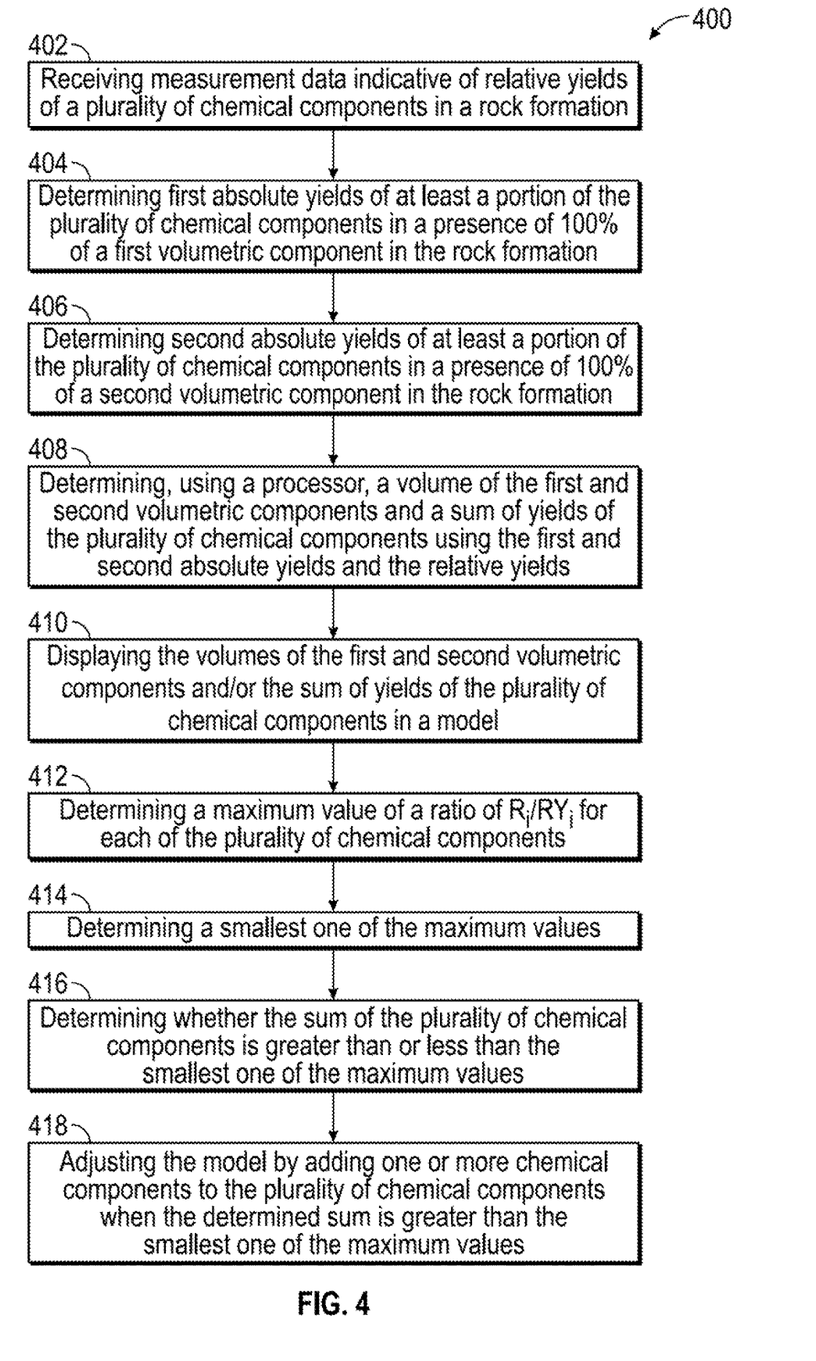
FIG. 4 illustrates a flowchart of a method for calculating and/or producing the geomechanical log model shown in FIG. 3.

FIG. 4 illustrates a flowchart of a method 400 for calculating, and/or producing a geomechanical log model, such as the geomechanical log model 100 shown in FIG. 3, according to an embodiment. The method 400 may include receiving measurement data indicative of relative yields of a plurality of chemical components in a rock formation, as shown at 402. First absolute yields of at least a portion of the plurality of chemical components may then be determined (e.g., referenced in a database) in a presence of 100% of a first volumetric component (e.g., calcite) in the rock formation, as shown at 404. Second absolute yields of at least a portion of the plurality of chemical components may then be determined (e.g., referenced in a database) in a presence of 100% of a second volumetric component (e.g., quartz) in the rock formation, as shown at 406. The volume of the first and second volumetric components and the sum of the yields of the plurality of chemical components may then be determined (e.g., with a processor) using the first and second absolute yields and the relative yields, as shown at 408. The volumes of the first and second volumetric components and/or the sum of the yields of the plurality of chemical components may then be displayed in a model, as shown at 410.

A maximum value of a ratio of $R_i/RY_i$ may be determined (e.g., using a processor) for each of the plurality of chemical components, as shown at 412. $R_i$ may represent the absolute yield of a particular chemical component in the plurality of chemical components, and $RY_i$ may represent a relative yield of the particular component. A smallest one of the maximum values may be determined, as shown at 414. It may then be determined whether the determined sum of the yields of the plurality of chemical components is greater than or less than the smallest one of the maximum values, as shown at 416. If the determined sum is greater than the smallest one of the maximum values, the model may be adjusted by adding one or more chemical components to the plurality of chemical components, as shown at 418.

Figure 5:
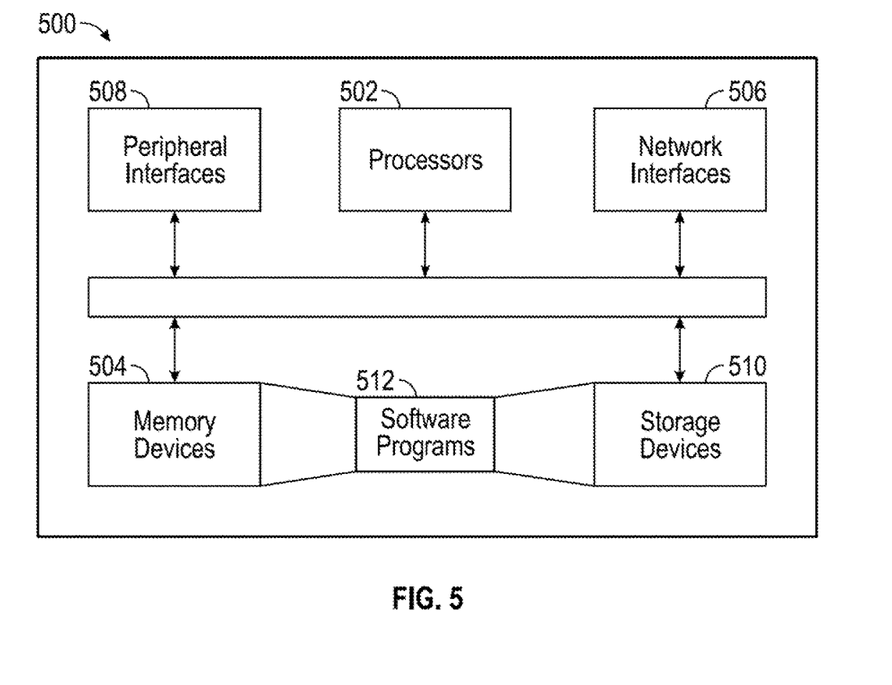
FIG. 5 illustrates a schematic view of a computer or processor system for calculating and/or producing the geochemical log model shown in FIG. 3, according to an embodiment.

Embodiments of the disclosure may also include one or more systems for implementing one or more embodiments of the method of the present disclosure. FIG. 5 illustrates a schematic view of a computer or processor system 500 for calculating and/or producing a geochemical log model, such as the geochemical log model 100 shown in FIG. 3, according to an embodiment. The processor system 500 may include one or more processors 502 of varying core (including multi-core) configurations and clock frequencies. The one or more processors 502 may be operable to execute instructions, apply logic, etc. It may be appreciated that these functions may be provided by multiple processors or multiple cores on a single chip operating in parallel and/or communicably linked together.

The processor system 500 may also include a memory system, which may be or include one or more memory devices and/or computer-readable media 504 of varying physical dimensions, accessibility, storage capacities, etc. such as flash drives, hard drives, disks, random access memory, etc., for storing data, such as images, files, and program instructions for execution by the processor 502. In an embodiment, the computer-readable media 504 may store instructions that, when executed by the processor 502, are configured to cause the processor system 500 to perform operations. For example, execution of such instructions may cause the processor system 500 to implement one or more portions and/or embodiments of the method described above.

The processor system 500 may also include one or more network interfaces 506. The network interfaces 506 may include any hardware, applications, and/or other software. Accordingly, the network interfaces 506 may include Ethernet adapters, wireless transceivers, PCI interfaces, and/or serial network components, for communicating over wired or wireless media using protocols, such as Ethernet, wireless Ethernet, etc.

The processor system 500 may further include one or more peripheral interfaces 508, for communication with a display screen, projector, keyboards, mice, touchpads, sensors, other types of input and/or output peripherals, and/or the like. In some implementations, the components of processor system 500 may not be enclosed within a single enclosure or even located in close proximity to one another, but in other implementations, the components and/or others may be provided in a single enclosure.

The memory device 504 may be physically or logically arranged or configured to store data on one or more storage devices 510. The storage device 510 may include one or more file systems or databases in any suitable format. The storage device 510 may also include one or more software programs 512, which may contain interpretable or executable instructions for performing one or more of the disclosed processes. When requested by the processor 502, one or more of the software programs 512, or a portion thereof, may be loaded from the storage devices 510 to the memory devices 504 for execution by the processor 502.

Those skilled in the art will appreciate that the above-described componentry is merely one example of a hardware configuration, as the processor system 500 may include any type of hardware components, including any accompanying firmware or software, for performing the disclosed implementations. The processor system 500 may also be implemented in part or in whole by electronic circuit components or processors, such as application-specific integrated circuits (ASICs) or field-programmable gate arrays (FPGAs).

The foregoing description of the present disclosure, along with its associated embodiments and examples, has been presented for purposes of illustration only. It is not exhaustive and does not limit the present disclosure to the precise form disclosed. Those skilled in the art will appreciate from the foregoing description that modifications and variations are possible in light of the above teachings or may be acquired from practicing the disclosed embodiments.

For example, the same techniques described, herein with reference to the processor system 500 may be used to execute programs according to instructions received from another program or from another processor system altogether. Similarly, commands may be received, executed, and their output returned entirely within the processing and/or memory of the processor system 500. Accordingly, neither a visual interface command terminal nor any terminal at all is strictly necessary for performing the described embodiments.

Likewise, the steps described need not be performed in the same sequence discussed or with the same degree of separation. Various steps may be omitted, repeated, combined, or divided, as necessary to achieve the same or similar objectives or enhancements. Accordingly, the present disclosure is not limited to the above-described embodiments, but instead is defined by the appended claims in light of their full scope of equivalents. Further, in the above description and in the below claims, unless specified otherwise, the term "execute" and its variants are to be interpreted as pertaining to any operation of program code or instructions on a device, whether compiled, interpreted, or run using other techniques.

What is claimed is:

1. A method for determining relative geochemical data, comprising:
   receiving measurement data that was measured by a downhole logging tool, wherein the measurement data represents relative yields of a plurality of chemical elements in a rock formation;
   determining first absolute yields of at least a portion of the plurality of chemical elements in a first chemical compound in the rock formation;
   determining second absolute yields of at least a portion of the plurality of chemical elements in a second chemical compound in the rock formation;
   determining, using a processor, a volume of the first chemical compound, a volume of the second chemical compound, and a sum of yields of the plurality of chemical elements using the first and second absolute yields and the relative yields, wherein determining the sum of yields of the plurality of chemical elements further comprises:
     determining a denominator based on the relative yield of a first chemical element in the plurality of chemical elements;
     determining a numerator based on a product of the absolute yield of the first chemical element in the first chemical compound and the volume of the first chemical compound; and
     determining the sum of yields based on the numerator divided by the denominator; and
   producing a geochemical log model that displays the volume of the first chemical compound, the volume of the second chemical compound, and the sum of the yields of the plurality of chemical elements.

2. The method of claim 1, wherein the volumes of the first and second chemical compounds and the sum of yields of the plurality of chemical elements are determined simultaneously.

3. The method of claim 2, wherein the volumes of the first and second chemical compounds and the sum of yields of the plurality of chemical elements are determined in an inverse model when the relative yields are combined with other inputs.

4. The method of claim 1, wherein determining the sum of yields of the plurality of chemical elements further comprises replacing the yields of the plurality of chemical elements with a single unknown variable.

5. The method of claim 3, further comprising displaying the relative yields for the plurality of chemical elements in the inverse model.

6. The method of claim 1, further comprising determining a maximum value of a ratio of $R_i/RY_i$ for each of the plurality of chemical elements, wherein $R_i$ represents the absolute yield of a particular chemical element in the plurality of chemical elements, and wherein $RY_i$ represents the relative yield of the particular element.

7. The method of claim 6, further comprising:
determining a smallest one of the maximum values; and
determining whether the sum of yields of the plurality of chemical elements is less than or equal to the smallest one of the maximum values.

8. The method of claim 7, further comprising determining that an inverse model is invalid when the smallest one of the maximum values is less than the sum of yields of the plurality of chemical elements.

9. The method of claim 8, further comprising receiving additional measurement data indicative of relative yields of one or more additional chemical elements, thereby causing the smallest one of the maximum values to be greater than or equal to the determined sum of yields of the plurality of chemical elements.

10. The method of claim 1, wherein the first and second chemical compounds are different.

11. The method of claim 1, wherein the first chemical compound comprises a first type of rock, the second chemical compound comprises a second type of rock, and the first and second types of rocks are different.

12. A non-transitory computer readable medium storing instructions thereon that, when executed by a processor, cause the processor to perform operations, the operations comprising:
receiving measurement data that was measured by a downhole logging tool, wherein the measurement data represents relative yields of a plurality of chemical elements in a rock formation;
determining first absolute yields of at least a portion of the plurality of chemical elements in a first chemical compound in the rock formation;
determining second absolute yields of at least a portion of the plurality of chemical elements in a second chemical compound in the rock formation;
determining, using a processor, a volume of the first chemical compound, a volume of the second chemical compound, and a sum of yields of the plurality of chemical elements using the first and second absolute yields and the relative yields, wherein determining the sum of yields of the plurality of chemical elements further comprises:
determining a denominator based on the relative yield of a first chemical element in the plurality of chemical elements;
determining a numerator based on a product of the absolute yield of the first chemical element in the first chemical compound and the volume of the first chemical compound; and
determining the sum of yields based on the numerator divided by the denominator; and
producing a geochemical log model that displays the volume of the first chemical compound, the volume of the second chemical compound, and the sum of the yields of the plurality of chemical elements.

13. The non-transitory computer readable medium of claim 12, wherein the volumes of the first and second chemical compounds and the sum of yields of the plurality of chemical elements are determined simultaneously in an inverse model when the relative yields are combined with other inputs.

14. The non-transitory computer readable medium of claim 12, wherein determining the sum of yields of the plurality of chemical elements further comprises replacing the yields of the plurality of chemical elements with a single unknown variable.

15. The non-transitory computer readable medium of claim 12, wherein the operations further comprise determining a maximum value of a ratio of $R_i/RY_i$ for each of the plurality of chemical elements, wherein $R_i$ represents the absolute yield of a particular chemical element in the plurality of chemical elements, and wherein $RY_i$ represents the relative yield of the particular element.

16. The non-transitory computer readable medium of claim 15, wherein the operations further comprise:
determining a smallest one of the maximum values; and
determining whether the sum of yields of the plurality of chemical elements is less than or equal to the smallest one of the maximum values.

17. A computing system, comprising:
one or more processors; and
a memory system comprising one or more computer-readable media storing instructions thereon that, when executed by at least one of the one or more processors, cause the computing system to perform operations, the operations comprising:
receiving measurement data that was measured by a downhole logging tool, wherein the measurement data represents relative yields of a plurality of chemical elements in a rock formation;
determining first absolute yields of at least a portion of the plurality of chemical elements in a first chemical compound in the rock formation;
determining second absolute yields of at least a portion of the plurality of chemical elements in a second chemical compound in the rock formation;
determining, using a processor, a volume of the first chemical compound, a volume of the second chemical compound, and a sum of yields of the plurality of chemical elements using the first and second absolute yields and the relative yields, wherein determining the sum of yields of the plurality of chemical elements further comprises:
determining a denominator based on the relative yield of a first chemical element in the plurality of chemical elements;
determining a numerator based on a product of the absolute yield of the first chemical element in the first chemical compound and the volume of the first chemical compound; and
determining the sum of yields based on the numerator divided by the denominator; and
producing a geochemical log model that displays the volume of the first chemical compound, the volume of the second chemical compound, and the sum of the yields of the plurality of chemical elements.

18. The computing system of claim 17, wherein the volumes of the first and second chemical compounds and the sum of yields of the plurality of chemical elements are determined simultaneously in an inverse model when the relative yields are combined with other inputs.

19. The computing system of claim 17, wherein determining the sum of yields of the plurality of chemical elements further comprises replacing the yields of the plurality of chemical elements with a single unknown variable.

20. The computing system of claim 17, wherein the operations further comprise determining a maximum value of a ratio of $R_i/RY_i$ for each of the plurality of chemical elements, wherein $R_i$ represents the absolute yield of a particular chemical element in the plurality of chemical elements, and wherein $RY_i$ represents the relative yield of the particular element.

21. The computing system of claim 17, wherein the operations further comprise:
   determining a smallest one of the maximum values; and
   determining whether the sum of yields of the plurality of chemical elements is less than or equal to the smallest one of the maximum values.

* * * * *